(12) United States Patent
Inoue et al.

(10) Patent No.: US 9,244,524 B2
(45) Date of Patent: Jan. 26, 2016

(54) SURGICAL INSTRUMENT AND CONTROL METHOD THEREOF

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/169,675

(22) Filed: Jan. 31, 2014

(65) Prior Publication Data

US 2014/0148819 A1 May 29, 2014

Related U.S. Application Data

(63) Continuation of application No. PCT/JP2012/070576, filed on Aug. 6, 2012.

(60) Provisional application No. 61/515,203, filed on Aug. 4, 2011.

(30) Foreign Application Priority Data

Feb. 16, 2012 (JP) .................................. 2012-031959

(51) Int. Cl.
*G06F 19/00* (2011.01)
*G06F 3/01* (2006.01)
(Continued)

(52) U.S. Cl.
CPC . *G06F 3/01* (2013.01); *A61B 17/29* (2013.01); *A61B 17/32002* (2013.01);
(Continued)

(58) Field of Classification Search
CPC ................... A61B 18/1442; A61B 2019/2242; A61B 2017/00867; A61B 2019/465; A61B 2019/2211; A61B 2018/00619; A61B 2018/00404; A61B 19/2203; A61B 2018/00345; C08L 2201/12

USPC ......... 700/245, 253, 257, 258, 259, 260, 261, 700/262, 264; 318/568.11, 568.12, 568.14, 318/568.16, 568.21; 901/1, 2, 8, 9, 30, 31, 901/34, 46; 606/1, 205
See application file for complete search history.

(56) References Cited

U.S. PATENT DOCUMENTS 4,830,569 A 5/1989 Jannborg
5,214,969 A 6/1993 Adkins et al.
(Continued)

FOREIGN PATENT DOCUMENTS

CN 101027010 A 8/2007
CN 101426412 A 5/2009
(Continued)

OTHER PUBLICATIONS

English Abstract of JP 01-234140 dated Sep. 19, 1989.
(Continued)

*Primary Examiner* — Dalena Tran
*Assistant Examiner* — Jaime Figueroa
(74) *Attorney, Agent, or Firm* — Scully, Scott, Murphy & Presser, PC

(57) ABSTRACT

A surgical instrument includes an end effector, a manipulation unit, a grip detecting unit, a driving unit, and a control unit. When the control unit determines that the end effector is applying the acting force to the target based on the information acquired by the grip detecting unit, the control unit sets an acting force increasing zone of a predetermined range in a first movable range in the first direction of the manipulation unit, sets a neutral zone in a remaining area of the first movable range, controls the driving unit so that the acting force increases with a constant gradient with respect to an amount of manipulation of the manipulation unit in the acting force increasing zone, and controls the driving unit so that the acting force is kept constant regardless of the amount of manipulation of the manipulation unit in the neutral zone.

7 Claims, 13 Drawing Sheets

(51) Int. Cl.
*A61B 19/00* (2006.01)
*B25J 9/16* (2006.01)
*A61B 17/29* (2006.01)
*A61B 17/32* (2006.01)
*A61B 18/14* (2006.01)
*A61B 19/08* (2006.01)
*B25J 13/02* (2006.01)
*A61B 17/068* (2006.01)
*A61B 19/10* (2006.01)
*A61B 17/00* (2006.01)

(52) U.S. Cl.
CPC .......... *A61B 18/1402* (2013.01); *A61B 19/081* (2013.01); *A61B 19/22* (2013.01); *A61B 19/2203* (2013.01); *A61B 19/26* (2013.01); *A61B 19/44* (2013.01); *B25J 9/1612* (2013.01); *B25J 9/1689* (2013.01); *B25J 13/02* (2013.01); *A61B 17/068* (2013.01); *A61B 19/10* (2013.01); *A61B 19/5244* (2013.01); *A61B 19/56* (2013.01); *A61B 2017/00119* (2013.01); *A61B 2017/00477* (2013.01); *A61B 2017/00482* (2013.01); *A61B 2019/2223* (2013.01); *A61B 2019/2269* (2013.01); *A61B 2019/2292* (2013.01); *A61B 2019/2296* (2013.01); *A61B 2019/465* (2013.01); *A61B 2019/467* (2013.01); *A61B 2019/4815* (2013.01); *A61B 2019/4868* (2013.01); *A61B 2019/4873* (2013.01); *A61B 2019/5255* (2013.01); *A61B 2019/5289* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | |
|---|---|---|
| 5,603,723 A | 2/1997 | Aranyi et al. |
| 5,632,432 A * | 5/1997 | Schulze et al. ............. 227/176.1 |
| 5,649,956 A | 7/1997 | Jensen et al. |
| 5,656,903 A * | 8/1997 | Shui et al. ................ 318/568.1 |
| 5,712,543 A | 1/1998 | Sjostrom |
| 5,762,458 A | 6/1998 | Wang et al. |
| 5,836,869 A | 11/1998 | Kudo et al. |
| 5,855,583 A | 1/1999 | Wang et al. |
| 5,871,493 A | 2/1999 | Sjostrom et al. |
| 6,007,550 A | 12/1999 | Wang et al. |
| 6,063,095 A | 5/2000 | Wang et al. |
| 6,090,122 A | 7/2000 | Sjostrom et al. |
| 6,102,850 A | 8/2000 | Wang et al. |
| 6,132,368 A | 10/2000 | Cooper |
| 6,132,441 A | 10/2000 | Grace |
| 6,206,903 B1 * | 3/2001 | Ramans .................... 606/205 |
| 6,246,200 B1 | 6/2001 | Blumenkranz et al. |
| 6,328,752 B1 | 12/2001 | Sjostrom et al. |
| 6,346,072 B1 | 2/2002 | Cooper |
| 6,430,473 B1 | 8/2002 | Lee et al. |
| 6,436,107 B1 | 8/2002 | Wang et al. |
| 6,441,577 B2 | 8/2002 | Blumenkranz et al. |
| 6,557,558 B1 | 5/2003 | Tajima et al. |
| 6,574,355 B2 | 6/2003 | Green |
| 6,587,750 B2 | 7/2003 | Gerbi et al. |
| 6,602,185 B1 | 8/2003 | Uchikubo |
| 6,645,196 B1 | 11/2003 | Nixon et al. |
| 6,666,876 B2 | 12/2003 | Kawai et al. |
| 6,676,684 B1 | 1/2004 | Morley et al. |
| 6,685,698 B2 | 2/2004 | Morley et al. |
| 6,699,177 B1 | 3/2004 | Wang et al. |
| 6,746,443 B1 | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,186 B2 | 4/2013 | Itkowitz et al. |
| 8,496,647 B2 | 7/2013 | Blumenkranz et al. |
| 8,540,748 B2 | 9/2013 | Murphy et al. |
| 8,845,681 B2 | 9/2014 | Grace |
| 8,876,858 B2 | 11/2014 | Braun |
| 8,903,549 B2 | 12/2014 | Itkowitz et al. |
| 8,906,002 B2 | 12/2014 | Kishi et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033024 A1 | 2/2003 | Sunaoshi |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |
| 2004/0186624 A1 | 9/2004 | Oda et al. |
| 2004/0243147 A1 | 12/2004 | Lipow |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142825 A1 | 6/2007 | Prisco et al. |

(56) References Cited

U.S. PATENT DOCUMENTS

| | | |
|---|---|---|
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0163948 A1 | 6/2009 | Sunaoshi et al. |
| 2009/0171147 A1 | 7/2009 | Lee et al. |
| 2009/0182193 A1* | 7/2009 | Whitman et al. ............. 600/104 |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0106141 A1* | 5/2011 | Nakamura ................... 606/205 |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1* | 6/2011 | van den Dool et al. ........ 606/205 |
| 2011/0230894 A1* | 9/2011 | Simaan et al. ................. 606/130 |
| 2011/0238079 A1 | 9/2011 | Hannaford et al. |
| 2011/0282493 A1 | 11/2011 | Ortmaier |
| 2011/0288579 A1* | 11/2011 | Hyodo ......................... 606/205 |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2305144 A1 * | 4/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-093270 A | 4/2008 |
| JP | 2008-173724 A | 7/2008 |
| JP | 4129313 B2 | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |

(56) References Cited

FOREIGN PATENT DOCUMENTS

| | | | |
|---|---|---|---|
| JP | 2012-091310 | A | 5/2012 |
| WO | 97/16123 | A1 | 5/1997 |
| WO | 97/16124 | A1 | 5/1997 |
| WO | 97/29690 | A1 | 8/1997 |
| WO | 98/25666 | A1 | 6/1998 |
| WO | 00/51486 | A1 | 9/2000 |
| WO | 00/60421 | A2 | 10/2000 |
| WO | 03/049596 | A2 | 6/2003 |
| WO | 2006/111966 | A2 | 10/2006 |
| WO | 2007/047782 | A2 | 4/2007 |
| WO | 2007/075864 | A1 | 7/2007 |
| WO | 2007/111955 | A2 | 10/2007 |
| WO | 2007/126443 | A2 | 11/2007 |
| WO | 2007/138674 | A1 | 12/2007 |
| WO | 2008/038184 | A2 | 4/2008 |
| WO | 2008/108289 | A1 | 9/2008 |
| WO | 2009/034477 | A2 | 3/2009 |
| WO | 2009/089614 | A1 | 7/2009 |
| WO | 2010/006057 | A1 | 1/2010 |
| WO | 2010/109932 | A1 | 9/2010 |
| WO | 2011/025786 | A1 | 3/2011 |
| WO | 2011/060139 | A2 | 5/2011 |
| WO | 2011/060185 | A1 | 5/2011 |
| WO | 2011/085815 | A1 | 7/2011 |
| WO | 2012/042949 | A1 | 4/2012 |

OTHER PUBLICATIONS

International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
U.S. Office Action dated May 8, 2015 received in related U.S. Appl. No. 14/157,920.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Appl. No. 14/169,321.
Extended Supplementary European Search Report dated Mar. 27, 2015 from related European Application No. 12 82 0056.5.
Chinese Office Action dated Jun. 3, 2015 from related Chinese Application No. 2012800359263, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Office Action dated Sep. 16, 2015 received in related, U.S. Appl. No. 13/566,012.
Office Action dated Nov. 19, 2015 received in related U.S. Appl. No. 14/157,920.

* cited by examiner

FIG. 9
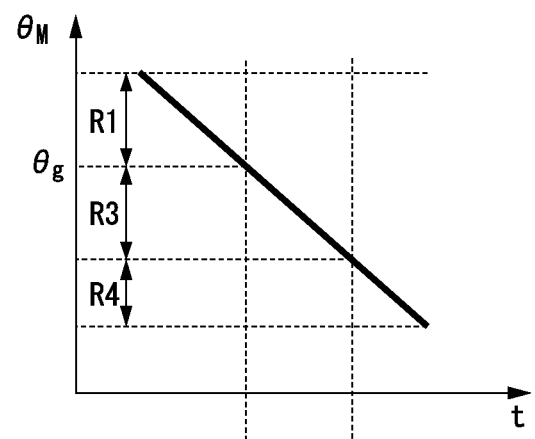
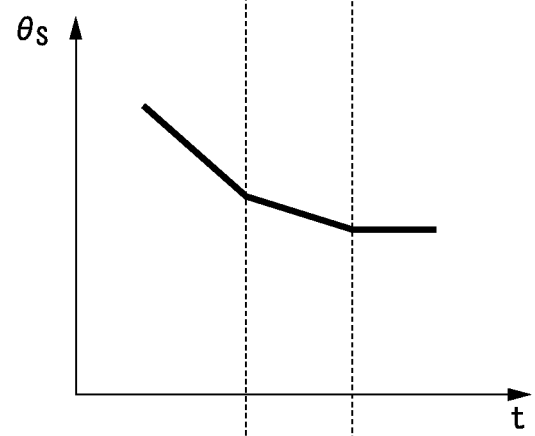
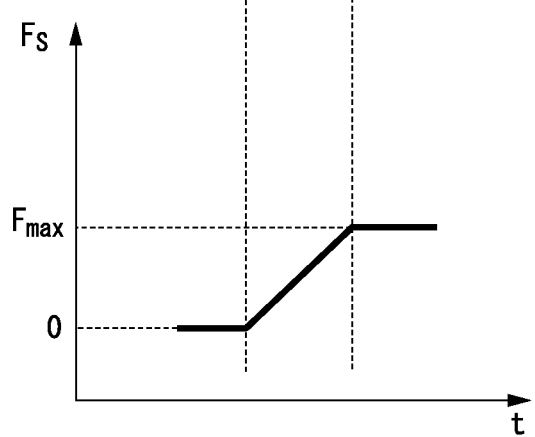

SURGICAL INSTRUMENT AND CONTROL METHOD THEREOF

This application is a continuation application based on PCT/JP2012/070576, filed on Aug. 6, 2012, claiming priority based on Japanese Patent Application No. 2012-031959, filed Feb. 16, 2012 and U.S. Patent Application No. 61/515,203, filed Aug. 4, 2011. The contents of the Japanese Patent Application, U.S. Patent Application and the PCT Application are incorporated herein by reference.

BACKGROUND OF THE INVENTION

1. Field of the Invention

The present invention relates to a surgical instrument having an end effector that is opened and closed and a control method thereof.

2. Description of Related Art

In the medical field, various surgical instruments are known. A surgical instrument having an end effector that is opened and closed is known as one of such surgical instruments. Since the end effector is used to grip or exclusion body tissue, it is important to appropriately control an acting force such as a gripping force or a displacing force that the end effector applies to the body tissue.

Japanese Unexamined Patent Application, First Publication No. 2010-076012 discloses a manipulator system as a surgical instrument in which a gripper as an end effector is driven with a motor. In this manipulator system, a gripping-start angle is recognized on the basis of the output of a gripping-start estimating observer. A control is performed so that the gripping force is increased after gripping is started and a desired gripping force is achieved when the opening angle of the gripper reaches the most closed angle.

SUMMARY OF THE INVENTION

According to a first aspect of the invention, a surgical instrument including: an end effector that is opened and closed; a manipulation unit configured to manipulate the end effector in a first direction so that the end effector applies an acting force to a target; a grip detecting unit configured to acquire an information used to determine whether the end effector applies the acting force to the target; a driving unit configured to drive the end effector to be opened and closed; and a control unit configured to control the driving unit based on the information input to the manipulation unit, when the control unit determines that the end effector applies the acting force to the target based on the information acquired by the grip detecting unit, the control unit sets an acting force increasing zone of a predetermined range in a first movable range in the first direction of the manipulation unit, sets a neutral zone in a remaining area of the first movable range, controls the driving unit so that the acting force increases with a constant gradient with respect to an amount of manipulation of the manipulation unit in the acting force increasing zone, and controls the driving unit so that the acting force is kept constant regardless of the amount of manipulation of the manipulation unit in the neutral zone.

According to a second aspect of the invention, in the first aspect, the acting force increasing zone may be set in an initial area toward the first direction in the first movable range.

According to a third aspect of the invention, in the first aspect or the second aspect, the grip detecting unit may include a camera imaging the end effector.

According to a fourth aspect of the invention, in any one of the first aspect to the third aspect, the grip detecting unit may include a force sensor detecting the acting force.

According to a fifth aspect of the invention, in any one of the first aspect to the fourth aspect, the first movable range of the manipulation unit may be set to be greater than a movable range of the end effector.

According to a sixth aspect of the invention, in the second aspect, the acting force may decrease when the manipulation unit is manipulated in a second direction, and when the manipulation unit may be manipulated in the second direction, the control unit may set an acting force decreasing zone of a predetermined range to an initial area toward the second direction in a second movable range of the second direction of the manipulation unit, and may control the driving unit so that the acting force decreases with a constant gradient with respect to the amount of manipulation of the manipulation unit in the acting force decreasing zone.

According to a seventh aspect of the invention, a control method of a surgical instrument having an end effector that is opened and closed and a manipulation unit configured to manipulate the end effector in a first direction so that the end effector applies an acting force to a target, the control method includes: repeatedly determining whether the end effector applies the acting force to the target; when determining that the end effector applies the acting force to the target, setting an acting force increasing zone of a predetermined range in a first movable range in the first direction of the manipulation unit, setting a neutral zone in a remaining area of the first movable range; causing the acting force to increase with a constant gradient with respect to an amount of manipulation of the manipulation unit in the acting force increasing zone; and causing the acting force to be kept constant regardless of the amount of manipulation of the manipulation unit in the neutral zone.

BRIEF DESCRIPTION OF THE DRAWINGS

FIG. 9 is an example of a graph illustrating the relationship of an opening angle of an opening and closing member, an opening angle of an end effector, and a gripping force in the medical master-slave manipulator.

DETAILED DESCRIPTION OF THE INVENTION

Figure 1:
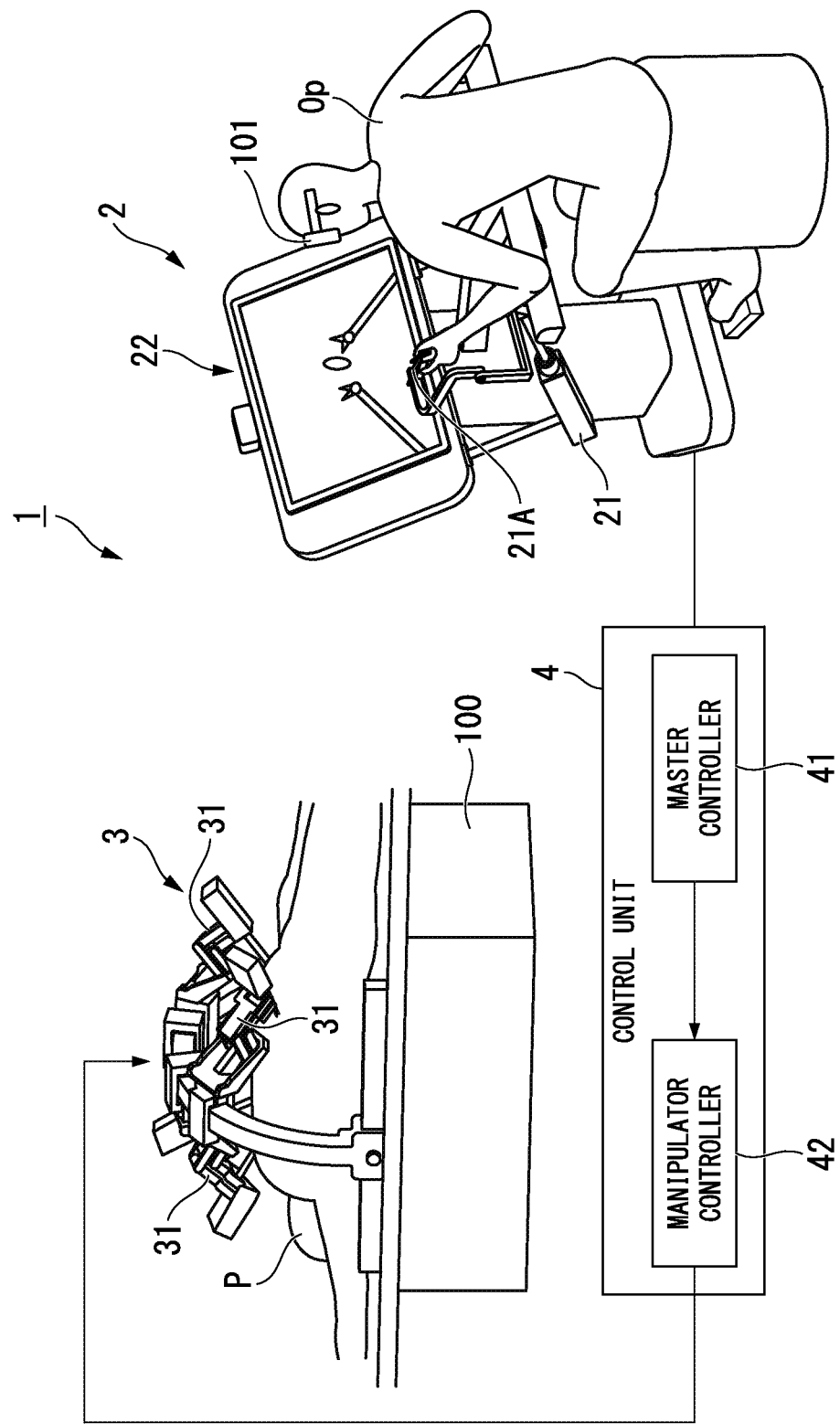
FIG. 1 is a diagram schematically illustrating the configuration of a medical master-slave manipulator according to a first embodiment of the invention.

Hereinafter, a first embodiment of the invention will be described. FIG. 1 is a diagram illustrating a medical master-slave manipulator (hereinafter, simply referred to as a "master-slave manipulator") 1 which is a surgical instrument according to this embodiment. The master-slave manipulator 1 includes a master input unit 2 having a master arm 21 and outputting a manipulation command and a slave manipulator 3 having a slave arm 31. The master-slave manipulator 1 remotely controls the slave arm 31 to follow the manipulation of the master arm 21 by an operator (user) Op. The manipulation command from the master arm 21 is transmitted to a master controller 41 of a control unit 4 and is input to a manipulator controller 42. Thereafter, a motion signal is sent from the manipulator controller 42 to the slave manipulator 3 and the slave arm 31 moves.

As shown in FIG. 1, the slave manipulator 3 is installed in an operating table 100 on which a patient P is placed and includes plural slave arms 31. Each slave arm has plural multi-degree-of-freedom joints and can move multi-axially. The multi-degree-of-freedom joints are individually driven by a power unit not shown. For example, a motor (servo motor) having a servo mechanism including an incremental encoder or a decelerator can be used as the power unit.

One of the plural slave arms 31 is provided with observation device not shown such as an endoscope that captures an image of the field of operation related to a manipulation target site and the other slave arm is provided with a treatment tool performing a variety of treatment to be described later. Known observation device can be appropriately selected and used as the observation device. Each slave arm includes a drive source that drives the treatment tool and the like. For example, a servo motor can be used as the drive source. In the following description, the slave arm provided with a treatment tool out of the slave arms may be also referred to as a "slave arm for treatment".

The master input unit 2 includes plural master arms 21 to be manipulated by an operator Op and a display unit 22 on which an image acquired by the observation device. Each master arm 21 has a known configuration which can multi-axially move and a grip section (manipulation unit) 21A which is gripped by the operator at a tip end close to the operator Op. The display unit 22 is constructed by a known display or the like and displays an image of a field of operation acquired by the observation device. In this embodiment, two images having a difference corresponding to parallax are projected onto the display unit 22 and the operator Op can stereoscopically view an image through the use of known 3D glasses 101 having a polarizing mechanism, a shutter mechanism, or the like.

Figure 2:
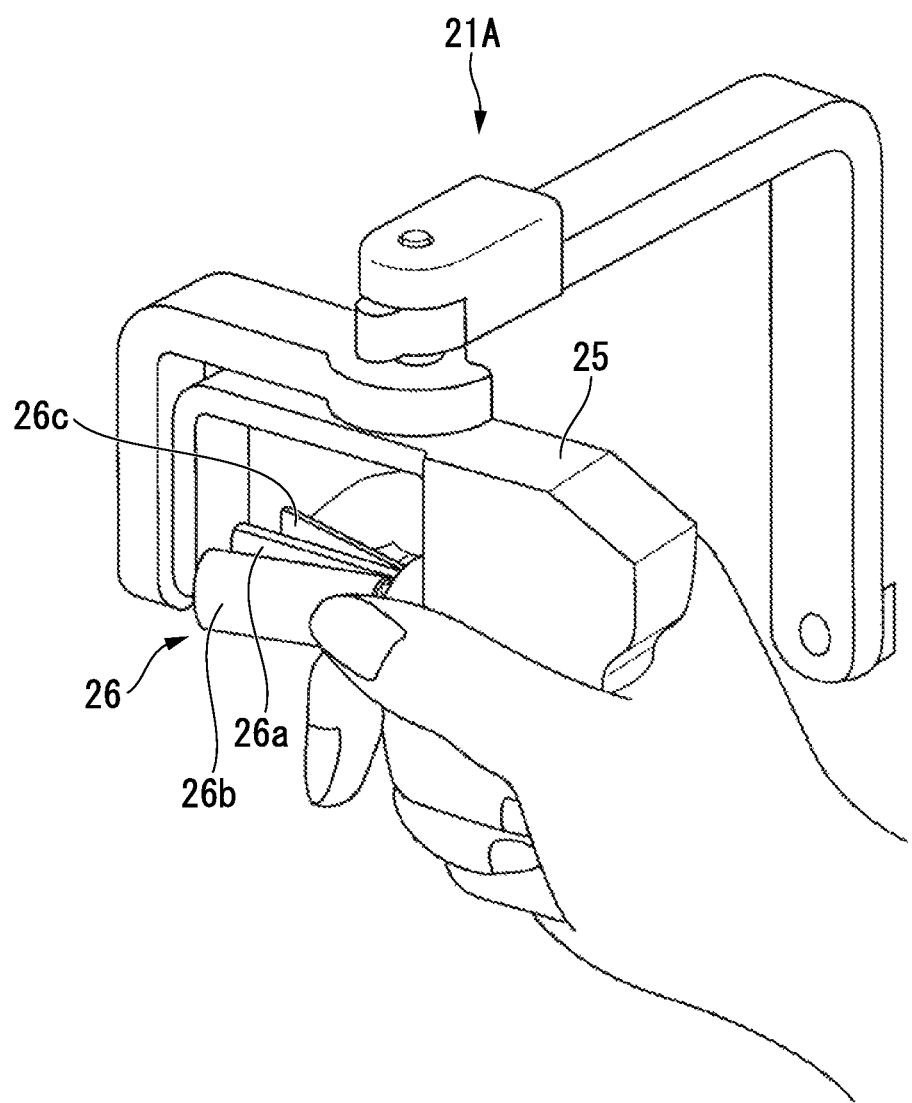
FIG. 2 is an enlarged view illustrating a grip section of the medical master-slave manipulator.

FIG. 2 is an enlarged view of the grip section 21A. The grip section 21A includes a grip body 25 to be gripped by the operator Op and an end effector manipulating part (manipulation unit) 26 to be opened and closed by the operator.

The operator Op grips the grip body 25 with his or her hand. The joints of the master arm 21 move with the change in the position and the orientation of the grip body 25, when the position and the orientation of the grip section 21A is changed with the movement of a wrist, an elbow, and a shoulder. The degrees of movement of the joints are detected by position detectors disposed around the joints and a manipulation signal corresponding to the degrees of movement is input to the master controller 41. Thereafter, the slave arm 31 corresponding to the master arm is driven in response to the signal sent from the manipulator controller 42, and the position and the orientation of the end effector of the treatment tool attached to the slave arm correspond to the position and the orientation of the grip body 25.

The end effector manipulating part 26 includes a base 26a and a pair of opening and closing members 26b and 26c opening and closing with respect to the base 26a at the same angle. The opening angle of the opening and closing members 26b and 26c about the base 26a is detected by detection device such as a encoder not shown and is transmitted to the master controller 41.

Figure 3:
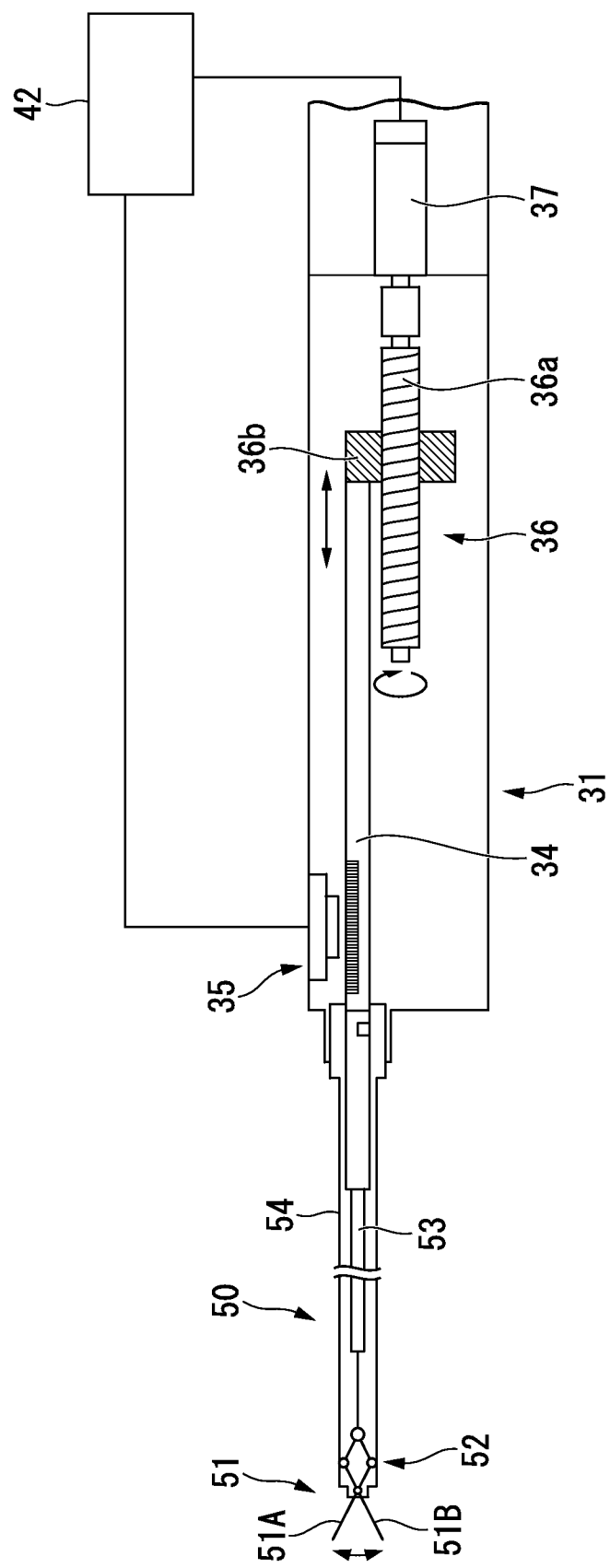
FIG. 3 is a diagram schematically illustrating the structure of a distal end of a slave arm in the medical master-slave manipulator.

FIG. 3 is a diagram schematically illustrating the structure of a distal end of the treatment slave arm 31. A treatment tool 50 is attached to the distal end of the treatment slave arm 31. In this embodiment, the treatment tool 50 is detachably attached to the treatment slave arm 31, but may not be attached and detached necessarily.

The treatment tool 50 includes an acting part (end effector) 51, a drive link 52, and a driving part 53 sequentially from the distal end directed to a body cavity of a patient P to the proximal end connected to the treatment slave arm 31. The drive link 52 and the driving part 53 are contained in a cylindrical chassis 54.

The acting part 51 includes, for example, a pair of jaws 51A and 51B that can be opened and closed. When the pair of jaws is closed, the acting part interposes and grips a target such as body tissue or a curved needle therebetween and applies a gripping force (acting force) to the target. The driving part 53 is a rod-shaped member and is connected to a drive rod (to be described later) in the slave arm 31 when the treatment tool 50 is connected to the slave arm 31. The driving part 53 advances or retreats a protopodite of the drive link 52 in the axis direction of the chassis 54 through driving force transmitted from the drive rod. Accordingly, the driving part 53 opens and closes the acting part 51. The drive link 52 connects the acting part 51 and the driving part 53 and a known link mechanism can be used.

A drive rod 34, a linear encoder 35, a linear driving mechanism 36, and a motor (driving unit) 37 are disposed at the distal end of the slave arm 31. The linear driving mechanism 36 has a known configuration including a ball screw 36a and a linear driving block 36b and converts the rotational movement of the motor 37 into the advance or retreat movement of the linear driving block 36b, which opens and closes the acting part 51. The proximal end of the drive rod 34 is connected to the linear driving block 36b, advances or retreats in the length direction thereof with the advance or retreat movement of the linear driving block 36b to cause the driving part 53 of the connected treatment tool 50 to advance or retreat. The amount of movement of the drive rod 34 is detected by the linear encoder 35.

Figure 4:
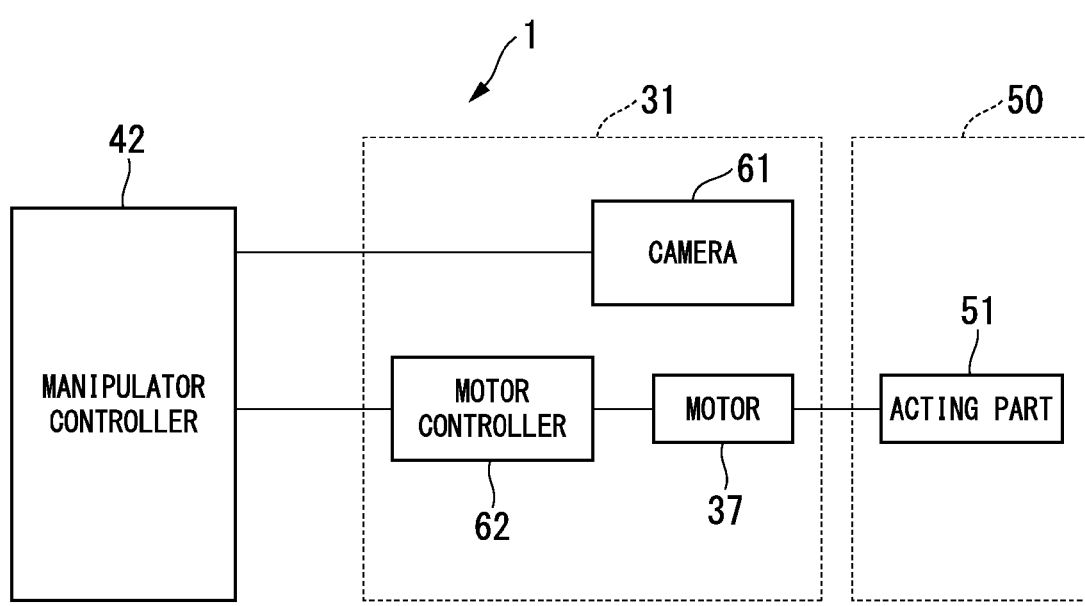
FIG. 4 is a block diagram illustrating the functional relation of a manipulator controller, a distal end of a slave arm, and a treatment tool in the medical master-slave manipulator.

FIG. 4 is a block diagram illustrating the functional relation of the manipulator controller 42, the distal end of the slave arm 31, and the treatment tool 50. Accordingly, connections to joints other than the manipulator controller 42 and the distal end of the slave arm are not shown.

A camera (grip detecting unit) 61 imaging the state of the acting part 51 of the treatment tool 50 and a motor controller 62 controlling the driving of the motor 37 based on input information input to the grip section 21A are disposed at the distal end of the slave arm 31. The camera 61 and the motor controller 62 are connected to the manipulator controller 42. The camera 61 images the acting part 51 at a predetermined time interval such as several tens of millimeter seconds (msec) and sequentially transmits the acquired images to the manipulator controller 42 as an information used to determine whether the acting part 51 grips a target. The motor controller 62 controls the current value applied to the motor 37 and the current application time in response to a command from the manipulator controller 42 and controls the magnitude of the driving force generated in the motor 37 and the driving time.

The operation of the master-slave manipulator 1 having the above-mentioned configuration will be described below.

An operator Op manipulates a master arm 21 to cause a corresponding treatment slave arm 31 to move and to cause the acting part 51 of the attached treatment tool 50 to approach a gripping target such as body tissue or a curved needle. When the operator grips the opening and closing members 26b and 26c of the end effector manipulating part 26 in a state where the gripping target is located between a pair of jaws 51A and 51B of the acting part 51, the angle (opening angle) formed by the opening and closing members 26b and 26c gradually decreases. This change is transmitted to the master controller 41 and the manipulator controller 42 as a detection value of the detection device. The manipulator controller 42 creates a control signal to be transmitted to the motor controller 62 based on the state of the end effector manipulating part 26 and the image transmitted from the camera 61, and transmits the created control signal to the motor controller 62. A mode of creating the control signal to be transmitted to the motor controller 62 will be described below in detail.

Figure 5:
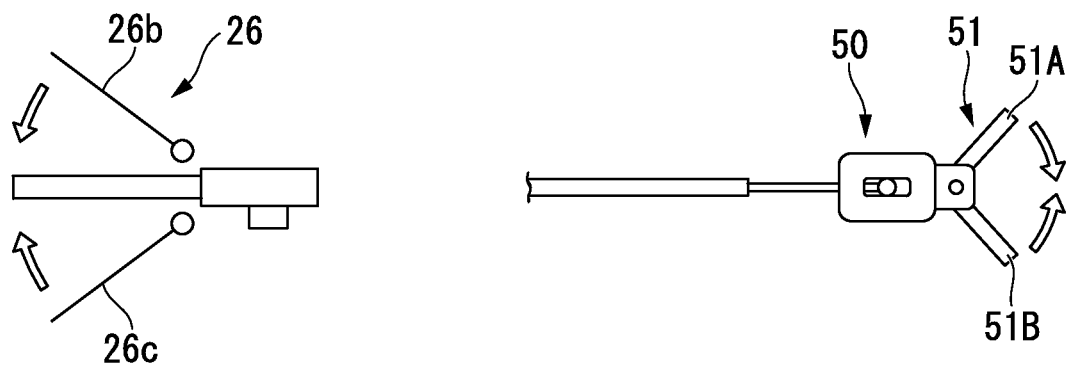
FIG. 5 is a diagram illustrating the correspondence of the manipulation on an end effector manipulating part and the movement of an acting part of a treatment tool.

The manipulator controller 42 sequentially processes the images transmitted from the camera 61 and repeatedly determines whether a target is gripped between a pair of jaws 51A and 51B. A control signal to be transmitted to the motor controller 62 is created so that the amount of manipulation on the end effector manipulating part 26 and the amount of opening and closing of the acting part 51 have predetermined correspondence until the pair of jaws 51A and 51B comes in contact with the target to grip the target between the pair of jaws 51A and 51B. As a result, as shown in FIG. 5, the pair of jaws 51A and 51B is closed in accordance with the amount of closing of the opening and closing members 26b and 26c of the end effector manipulating part 26. At this time, the variation in opening angle (hereinafter, also referred to as an "opening-closing member opening angle") of the opening and closing members 26b and 26c of the end effector manipulating part 26 the variation in opening angle of the pair of jaws 51A and 51B may correspond to each other in a one-to-one manner or may correspond to each other with a predetermined coefficient multiplied thereby.

In this embodiment, the opening angle of the pair of jaws 51A and 51B is controlled by controlling the driving of the motor 37 in response to the control signal to the motor controller 62. Alternatively, the opening angle of the pair of jaws may be controlled through an image process on the image acquired by the camera 61 or the opening angle of the pair of jaws may be controlled based on the detection value of the linear encoder 35.

Figure 6:
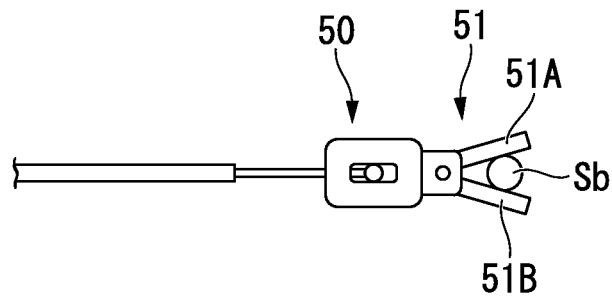
FIG. 6 is a diagram illustrating a state where the acting portion grips a target.

As shown in FIG. 6, when the manipulator controller 42 determines that a gripping target Sb comes in contact with the pair of jaws 51A and 51B and is gripped between the pair of jaws 51A and 51B, the manipulator controller 42 switches the mode of creating a control signal to be transmitted to the motor controller 62. The manipulator controller 42 compares the present value of the opening-closing member opening angle with the structural minimum value of the opening-closing member opening angle, sets a gripping force increasing zone of a predetermined range in a movable range (first movable range) in the closing direction (first direction) of the opening and closing members 26b and 26c at the gripping-start time point, and sets a neutral zone in the other range. The above-mentioned minimum value may be negative when the opening and closing members 26b and 26c can be further manipulated to the closing direction even after the opening and closing members 26b and 26c are parallel to the base 26a.

The "neutral zone" in the first embodiment of the invention means a zone in which a non-zero gripping force (acting force) applied to a target from the acting part 51 does not vary even when the opening and closing members 26b and 26c are manipulated in the movable range of the opening and closing members 26b and 26c.

In this embodiment, a predetermined angle range (for example, 30 degrees) from the minimum value of the opening angle of the opening and closing members is set as the "gripping force increasing zone" in which the opening-closing member opening angle is proportional to the gripping force, and the other angle range, that is, the angle range from the present opening-closing member opening angle to the gripping force increasing zone, is set as the neutral zone.

When the opening-closing member opening angle is in the neutral zone, the opening angle (hereinafter, also referred to as an "end effector opening angle") of the pair of jaws 51A and 51B continues to be controlled and the manipulator controller 42 controls the motor controller 62 so that the opening angle does not vary and the gripping force does not vary. For example, a control signal is created to apply low current of an extent not to increase the gripping force to the motor 37.

When an operator closes the opening and closing members 26b and 26c and the opening-closing member opening angle enters the gripping force increasing zone, the manipulator controller 42 creates a control signal so that the gripping force increases in proportion to the variation of the opening-closing member opening angle in the closing direction and the gripping force reaches a predetermined upper limit when the opening-closing member opening angle becomes the minimum value. In this embodiment, the control signal is created so that the current value increases as the opening and closing members 26b and 26c become closed based on the relational expression of a predetermined motor driving current value and the gripping force.

Figure 7:
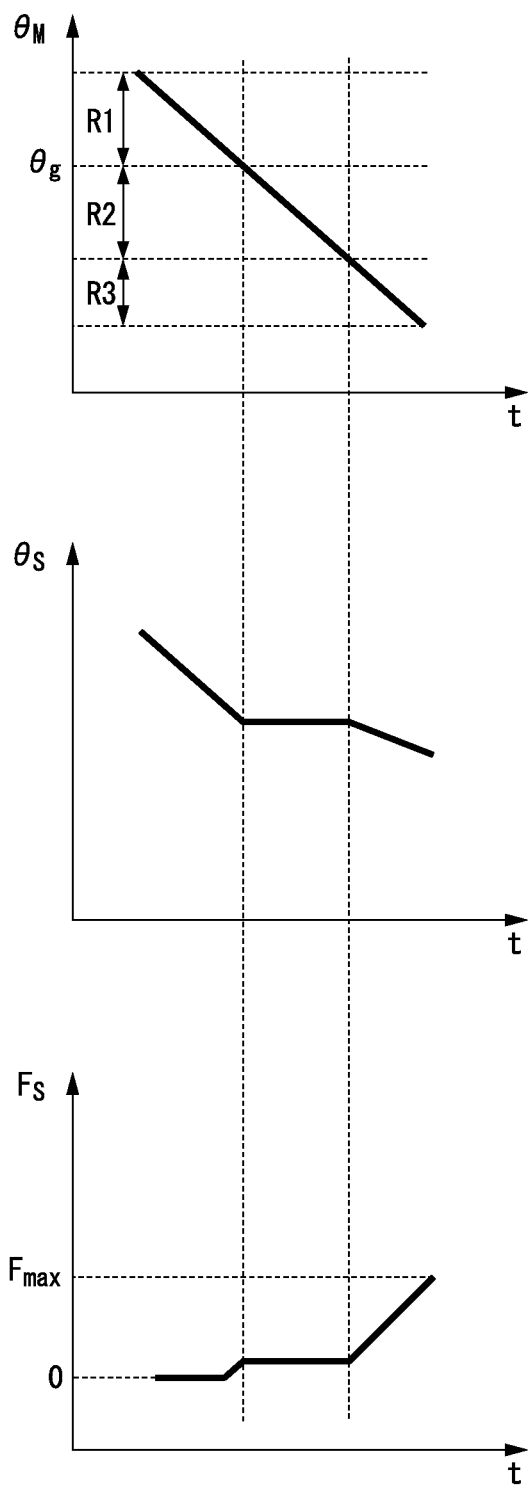
FIG. 7 is an example of a graph illustrating the relationship of an opening angle of an opening and closing member, an opening angle of an end effector, and a gripping force in the medical master-slave manipulator.

FIG. 7 is an example of a graph illustrating the relationship of the opening-closing member opening angle, the end effector opening angle, and the gripping force, where the opening-closing member opening angle $\theta_M$ is shown at the upper stage, the end effector opening angle $\theta_S$ is shown at the middle stage, and the gripping force $F_S$ is shown at the lower stage. In a first zone R1 before a target is gripped by the acting part 51 ($\theta_M$>opening angle $\theta_g$ at the gripping-start time) out of the movable range of the opening and closing members, the opening-closing member opening angle $\theta_M$ is proportional to the end effector opening angle $\theta_S$. In the first zone R1, since a target is not gripped, the gripping force $F_S$ is basically zero. A gripping force is slightly generated before and after the boundary between the first zone R1 in which a target is gripped and the neutral zone R2.

In the neutral zone R2 subsequent to the first zone R1, as the opening-closing member opening angle $\theta_M$ decreases, the end effector opening angle $\theta_S$ is constant and the gripping force FS does not increase but is kept constant.

In the gripping force increasing zone (acting force increasing zone) R3 subsequent to the neutral zone R2, as the opening-closing member opening angle $\theta_M$ decreases, the gripping force FS increases with a constant gradient and reaches the maximum gripping force $F_{max}$ at the end of the gripping force increasing zone R3. The behavior of the end effector opening angle $\theta_S$ in the gripping force increasing zone R3 varies depending on the rigidity of the gripping target. For example, when the rigidity is high, the target is not deformed and thus the end effector opening angle $\theta_S$ has a tendency to hardly vary. However, when the rigidity of the target is low, the target is deformed with the increase in gripping force and thus the end effector opening angle $\theta_S$ decreases by a predetermined degree depending on the rigidity.

As described above, in the master-slave manipulator 1 according to this embodiment, it is determined that the gripping of a target by the acting part 51 is started based on the image from the camera 61. Accordingly, the master controller 41 and the manipulator controller 42 of the control unit 4 controls the motor 37 to control the movement of the acting part 51 so that a predetermined angle range in the movable range of the end effector manipulating part 26 of the master arm 21 in the closing direction at that time is set to the gripping force increasing zone and the other range is set to the neutral zone. As a result, the gripping force applied to the acting part 51 when the end effector manipulating part 26 is manipulated in a predetermined angle range becomes the maximum gripping force $F_{max}$ and the gradient indicating the relationship between the amount of manipulation of the end effector manipulating part 26 and the amount of increase of the gripping force in the gripping force increasing zone is constant, regardless of the size of the gripping target.

Therefore, it is possible to provide a surgical instrument which can be suitably controlled so that the gripping force applied to the acting part 51 is not excessive and in which the operational feeling of an operator does not vary even when the gripping target is changed.

In the surgical instrument according to the embodiment of the invention, it is necessary to set the movable ranges of the manipulation unit (the end effector manipulating part 26) and the acting part 51 and the correspondence thereof so as to set the gripping force increasing zone of a predetermined angle range for the manipulation unit even when a possible smallest gripping target is gripped. For example, the movable angle range of the manipulation unit may be set to be greater than the movable range of the acting part 51, or the ratio of the amount of manipulation of the manipulation unit and the amount of opening and closing of the acting part 51 may be adjusted to set the acting part to be opened and closed by a predetermined multiple of the amount of manipulation of the manipulation unit. The specific example thereof is not particularly limited.

A second embodiment of the invention will be described below with reference to FIGS. 8 and 9. A master-slave manipulator 71 according to this embodiment is different from the master-slave manipulator 1, in the configuration of the grip detecting unit and the positional relation between the gripping force increasing zone and the neutral zone in the movable range of the manipulation unit. In the following description, the same elements as described above are referenced by the same reference numerals and description thereof will not be repeated.

Figure 8:
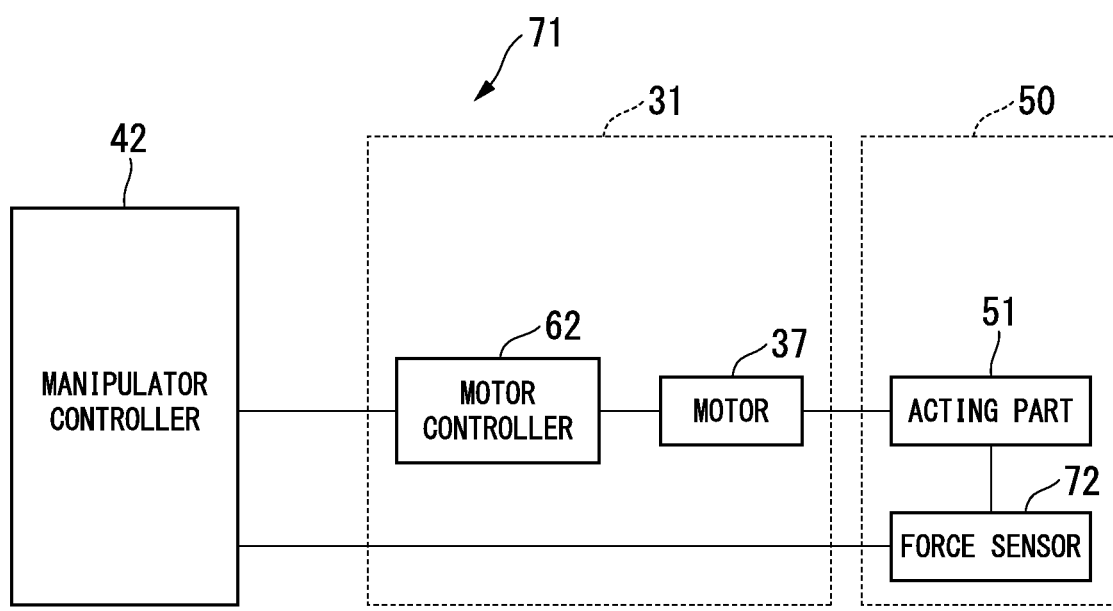
FIG. 8 is a block diagram illustrating the functional relation of a manipulator controller, a distal end of a slave arm, and a treatment tool in a medical master-slave manipulator according to a second embodiment of the invention.

FIG. 8 is a block diagram illustrating the functional relation of the manipulator controller 42, the distal end of the slave arm 31, and the treatment tool 50 in the master-slave manipulator 71. In FIG. 8, similarly to FIG. 4, connections to joints other than the manipulator controller 42 and the distal end of the slave arm are not shown.

In this embodiment, the slave manipulator 31 does not include a camera 61. On the other hand, a force sensor 72 detecting a gripping force applied between a pair of jaws 51A and 51B is provided as the grip detecting unit to the acting part 51 of the treatment tool 50. The value detected by the force sensor 72 is sequentially transmitted to the manipulator controller 42.

The operation of the master-slave manipulator 71 according to this embodiment will be described below.

The manipulator controller 42 determines that a target is gripped between a pair of jaws 51A and 51B when the force sensor 72 starts detecting of the gripping force (when the gripping force becomes non-zero) with normal reference to the value detected by the force sensor 72.

FIG. 9 is an example of a graph illustrating the relationship of the opening-closing member opening angle, the end effector opening angle, and the gripping force in the master-slave manipulator 71, and the display pattern thereof is substantially the same as shown in FIG. 7. In this embodiment, the manipulator controller 42 sequentially sets the gripping force increasing zone R3 and the neutral zone R4 in the closing direction of the opening and closing members 26b and 26c in the movable range (first movable range). Specifically, as shown in FIG. 9, the gripping force increasing zone R3 of a predetermined angle range is set just after the first zone R1. Accordingly, the manipulator controller 42 creates a control signal and transmits the created control signal to the motor controller 62, so that as the opening-closing member opening angle $\theta_M$ decreases after it is determined that a target is gripped between a pair of jaws 51A and 51B, the gripping force $F_S$ increases with a constant gradient and reaches the maximum gripping force $F_{max}$ at the end of the gripping force increasing zone R3. The gripping force applied to the acting part 51 is controlled based on the value detected by the force sensor 72. A known feedback control may be applied to this control.

The movable range in the closing direction of the end effector manipulating part 26 after the value of the gripping force $F_S$ reaches $F_{max}$ is the neutral zone R4. In the neutral zone R4, the gripping force FS is kept $F_{max}$ regardless of the decrease of the opening-closing member opening angle $\theta_M$. Since the manipulator controller 42 controls only the value of the gripping force $F_S$ based on the value detected by the force sensor 72, the manipulator controller does not directly control the end effector opening angle $\theta_S$, but the end effector opening angle $\theta_S$ is almost constant in the neutral zone R4.

In the master-slave manipulator 71 according to this embodiment, similarly to the master-slave manipulator 1 according to the first embodiment, it is possible to provide a surgical instrument which can be suitably controlled so that the gripping force applied to the acting part is not excessive and in which the operational feeling of an operator Op does not vary even when the gripping target is changed.

After it is determined that the gripping of a target is started, the gripping force increasing zone R3 is first set in the movable range in the closing direction of the end effector manipulating part 26. Accordingly, when the operator Op closes the end effector manipulating part 26 after gripping the target, the gripping force applied to the acting part 51 increases at once. Therefore, the operator Op can perform the manipulation more intuitively.

Since the gripping force $F_S$ in the gripping force increasing zone R3 is controlled based on the value detected by the force sensor 72 disposed in the acting part 51, it is possible to more accurately control the gripping force.

In this embodiment, the example in which the control of the gripping force is performed based on the value detected by the force sensor 72 is explained, but this configuration is not necessary. That is, although the accuracy is slightly low, it is also possible to control the gripping force by controlling a drive current value of the motor 37, similarly to the first embodiment.

A third embodiment of the invention will be described below with reference to FIG. 10. A master-slave manipulator according to this embodiment is different from the above-mentioned embodiments, in that a gripping force increasing zone and a neutral zone are set for the manipulation in addition to a control of the closing direction of the end effector manipulating part.

The mechanical structure of the master-slave manipulator according to this embodiment is the same as the master-slave manipulator 71 according to the second embodiment, and the control of the manipulation in the closing direction of the end effector manipulating part 26 is the same as in the second embodiment. In this embodiment, the manipulation in the opening direction (second direction) of the end effector manipulating part 26 is additionally subjected to a predetermined control.

Figure 10:
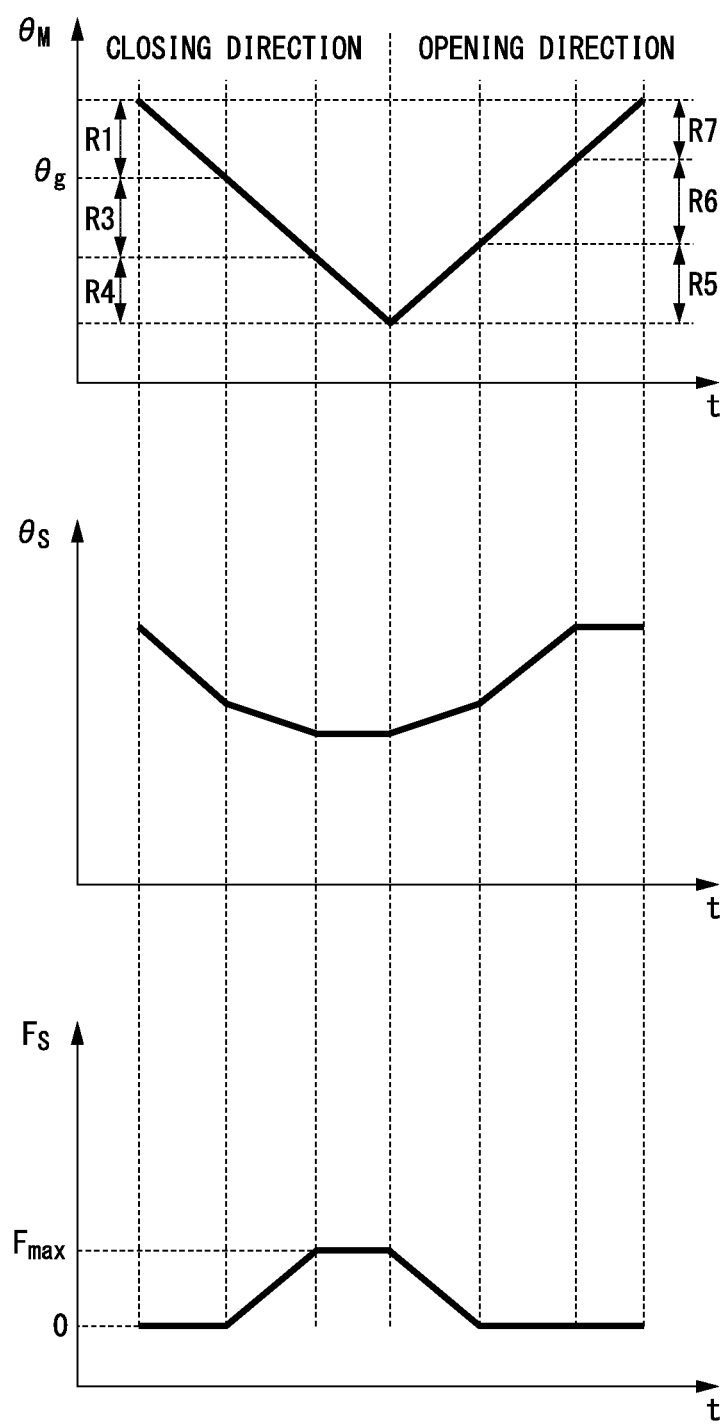
FIG. 10 is an example of a graph illustrating the relationship of an opening angle of an opening and closing member, an opening angle of an end effector, and a gripping force in a medical master-slave manipulator according to a third embodiment of the invention.

FIG. 10 is an example of a graph illustrating the relationship of the opening-closing member opening angle, the end effector opening angle, and the gripping force in the master-slave manipulator according to this embodiment, and the display pattern thereof is substantially the same as shown in FIG. 9. In FIG. 10, the relationship of the opening-closing member opening angle $\theta_M$, the end effector opening angle $\theta_S$, and the gripping force $F_S$ in the manipulation of the opening direction subsequently to the neutral zone R4 in the manipulation of the closing direction is shown.

When the gripping force FS decreases based on the value detected by the force sensor 72, the manipulator controller 42 determines that the manipulation of the end effector manipulating part 26 is performed in the opening direction and applies the control in the opening direction to creating a drive signal to the motor driver 62. As shown in FIG. 10, a gripping force decreasing zone (acting force decreasing zone) R5 of a predetermined range is first set as the initial zone in the opening direction in the movable range (second movable range) in the opening direction. In the gripping force decreasing zone R5, as the opening-closing member opening angle $\theta_M$ increases, the gripping force $F_S$ decreases with a constant gradient until the gripping force becomes zero.

Subsequently to the gripping force decreasing zone R5, a second zone R6 in which the end effector opening angle $\theta_S$ increases with a constant gradient with the increase of the opening-closing member opening angle $\theta_M$ is set. In the second zone R6, the acting part 51 is separated from a gripping target and the grip is released. Similarly to the first embodiment, the end effector opening angle $\theta_S$ in the second zone R6 is controlled by controlling the drive current of the motor 37. After the acting part 51 is opened to the maximum, the other movable range in the opening direction of the opening and closing members 26b and 26c is set to a margin zone R7 in which the acting part 51 does not move with the manipulation of the opening and closing members 26b and 26c.

The angle range of the gripping force decreasing zone R5 varies depending on the state of the end effector manipulating part 26 just before performing the manipulation in the opening direction. In the example shown in FIG. 10, since the end effector manipulating part 26 is manipulated in the closing direction up to the limit of the movable range including the neutral zone R4 and is then manipulated in the opening direction, the angle range of the gripping force decreasing zone R5 is matched with the gripping force increasing zone R3. For example, when the end effector manipulating part 26 is manipulated, for example, by 15 degrees in the closing direction up to the middle of the gripping force increasing zone R3 and is then manipulated in the opening direction, the angle range of the gripping force decreasing zone R5 is set to 15 degrees which is the same as the amount of manipulation in the closing direction in the gripping force increasing zone R2.

The gradient with which the gripping force decreases in the gripping force decreasing zone R5 is set to a value obtained by multiplying the gradient, with which the gripping force increases in the gripping force increasing zone R3, by −1. By employing this configuration, the operational feeling given to the operator Op when increasing and decreasing the gripping force can be made to be constant in both the opening direction and the closing direction of the end effector manipulating part 26.

In the master-slave manipulator according to this embodiment, similarly to the master-slave manipulators according to the above-mentioned embodiments, it is possible to provide a surgical instrument which can be suitably controlled so that the gripping force applied to the acting part is not excessive and in which the operational feeling of an operator Op does not vary even when the gripping target is changed.

The gripping force decreasing zone R5 is set just after the manipulation in the opening direction of the end effector manipulating part 26 is started, and the manipulator controller 42 performs a control so that the variation gradient of the gripping force becomes the value obtained by multiplying the gradient in the gripping force increasing zone by −1. Accordingly, even in the operation of alternately repeating the manipulation in the closing direction and the manipulation in the opening direction to finely adjust the gripping force of the acting part, it is possible to suitably maintain the operator Op' operational feeling.

In this embodiment, the example in which the gripping force decreasing zone R5 is set just after the manipulation in the opening direction of the end effector manipulating part 26 is started is explained, but the control in the opening direction is not limited to this configuration.

Figure 11:
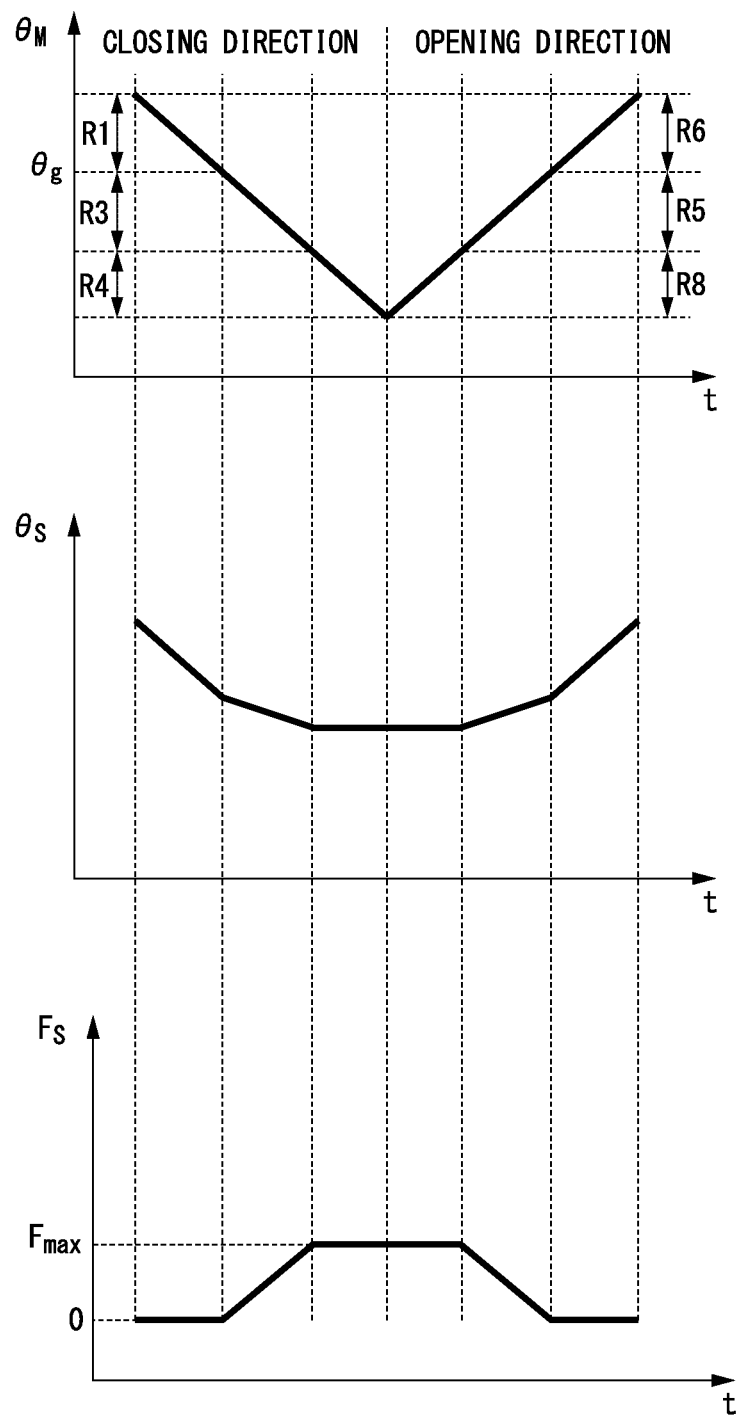
FIG. 11 is an example of a graph illustrating the relationship of an opening angle of an opening and closing member, an opening angle of an end effector, and a gripping force according to a modified example of the medical master-slave manipulator.

In a modified example shown in FIG. 11, since a neutral zone R8 is set just after the manipulation in the opening direction is started, the gripping force decreasing zone R5 and the second zone R6 are set subsequently thereto, the correspondence of the control details with the opening angle of the opening and closing members 26b and 26c is completely constant in both the closing direction and the opening direction. By employing this control, unlike FIG. 10, even when the manipulation in the opening direction is performed after the end effector manipulating part 26 is closed to the limit, the opening-closing member opening angle at the time of releasing the grip and the opening-closing member opening angle at the time of starting the grip are matched with each other.

Accordingly, this modified example is suitable for the case where the operator Op prefers the correspondence between the opening-closing member opening angle and the end effector opening angle as the operational feeling.

The information of the detection device disposed in the grip section 21A may be used instead of the value detected by the force sensor 72 to detect that the end effector manipulating part 26 is manipulated in the opening direction.

A fourth embodiment of the invention will be described below with reference to FIGS. 12 to 14. A master-slave manipulator according to this embodiment is different from the master-slave manipulator according to the above-mentioned embodiments, in the use pattern of the attached treatment tool.

Figure 12:
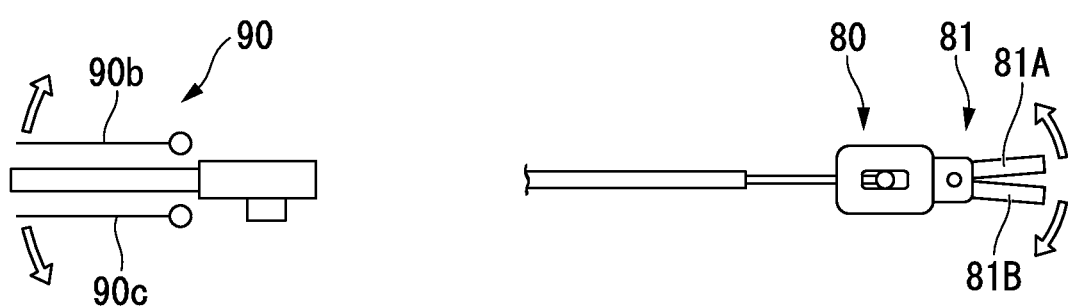
FIG. 12 is a diagram illustrating the correspondence of the manipulation on an end effector manipulating part and the movement of an acting part of a treatment tool in a medical master-slave manipulator according to a fourth embodiment of the invention.

FIG. 12 is a diagram schematically illustrating a treatment tool 80 and an end effector manipulating part 90 in this embodiment. An acting part 81 includes a pair of jaws 81A and 81B similarly to the above-mentioned treatment tool 50, but the pair of jaws 81A and 81B does not grip a target but is used to press and widen the target by opening. In correspondence therewith, a pair of opening and closing members 90b and 90c of the end effector manipulating part 90 is closed in the initial state and the operator Op opens the opening and closing members 90b and 90c to open the pair of jaws 81A and 81B. A hook may be appropriately provided to the pair of opening and closing members 90b and 90c so as to facilitate the opening manipulation.

In the master-slave manipulator according to this embodiment having the above-mentioned treatment tool 80 attached thereto, a pressing force acting on a target is controlled as an acting force by opening the pair of jaws 81A and 81B. Since the pressing force applied to the acting part 81 increases with the manipulation in the opening direction of the end effector manipulating part 90, the opening direction is the first direction.

Figure 13:
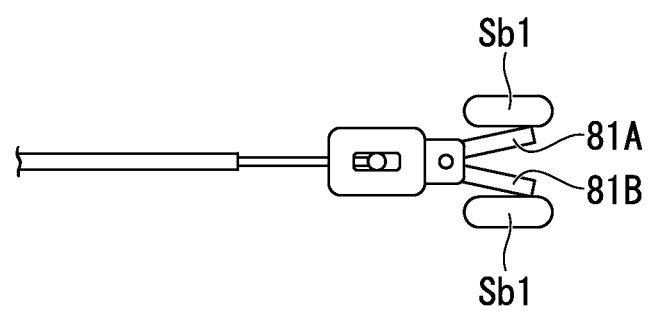
FIG. 13 is a diagram illustrating a state where the acting part presses a target.

In the master-slave manipulator according to this embodiment, as shown in FIG. 13, when a pressing target Sb1 comes in contact with the outside surfaces in the opening and closing direction of the pair of jaws 81A and 81B, the manipulator controller 42 determines that the pressing on the pressing target Sb1 is started. This determination may be performed using an image acquired with the camera or the like or may be performed based on the value detected by the force sensor or the like. However, since a widening treatment tool such as the treatment tool 80 often starts the pressing manipulation after the pair of jaws in a closed state is inserted into a gap between two tissues coming in contact therewith, it is not easy to determine the pressing start through the image process. Therefore, it is preferable that a reactive force acting on the pair of jaws from the pressing target be detected by the use of a force sensor or the like to determine that the start of the pressing.

Figure 14:
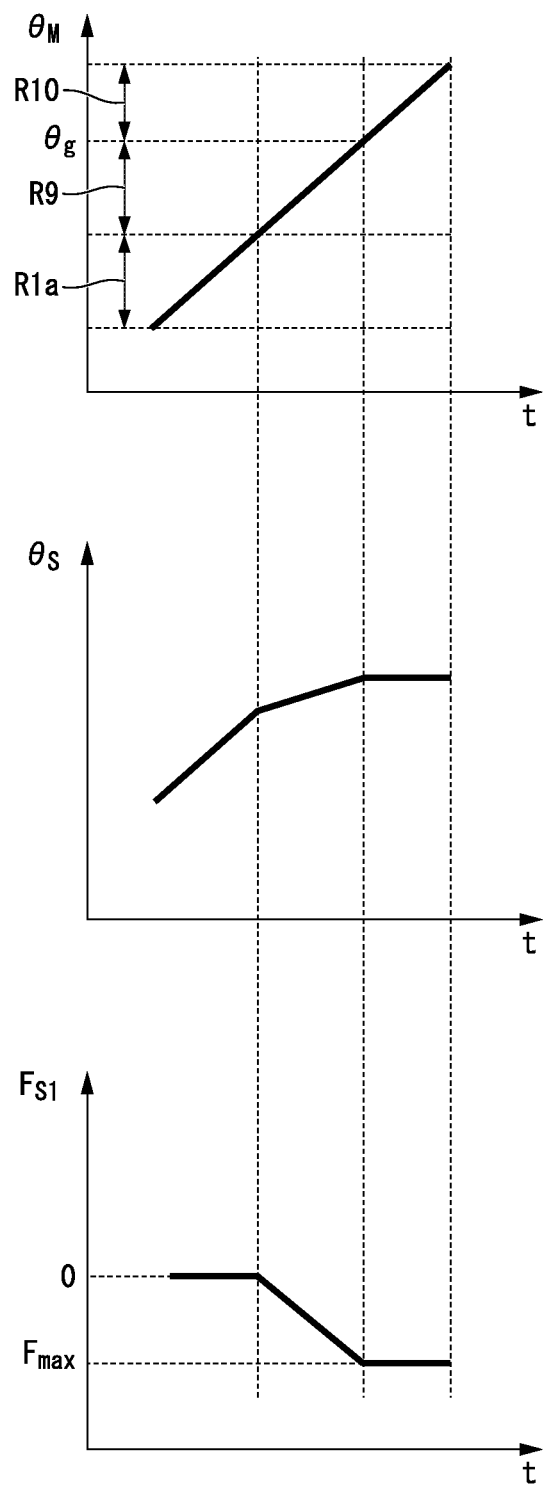
FIG. 14 is an example of a graph illustrating the relationship of an opening angle of an opening and closing member, an opening angle of an end effector, and a gripping force in the medical master-slave manipulator.

FIG. 14 is an example of a graph illustrating the relationship of the opening-closing member opening angle, the end effector opening angle, and the gripping force in the master-slave manipulator according to this embodiment. The display pattern thereof is substantially the same as shown in FIG. 9 or the like, but the pressing force $F_{S1}$ which is an acting force is a force acting in the opposite direction of the pressing force $F_S$ and is thus expressed by a negative value.

As shown in FIG. 14, the control in the opening direction of the pair of opening and closing members 90b and 90c is substantially the same as the control in the closing direction of the opening and closing members 90b and 90c in the second embodiment. That is, a first zone R1a in which the opening-closing member opening angle $\theta_M$ is proportional to the end effector opening angle $\theta_S$, a pressing force increasing zone R9 in which the pressing force increases to the maximum pressing force $F_{max}$ with a constant gradient, and a neutral zone R10 in which the pressing force is maintained in $F_{max}$ regardless of the value of the opening-closing member opening angle $\theta_M$ are sequentially set from the side on which the opening angle of the pair of opening and closing members 90b and 90c is the smallest.

Accordingly, when the pair of opening and closing members 90b and 90c is manipulated in the opening direction by a predetermined angle range from the time point at which the pressing is started, the correspondence between the amount of manipulation of the opening and closing members 90b and 90c and the pressing force is controlled so that the value of the pressing force becomes the maximum pressing force $F_{max}$. As a result, it is possible to maintain a predetermined operational feeling regardless of the type of the pressing target.

In this way, the surgical instrument and the control method thereof according to the above-mentioned embodiments of the invention can be applied to a surgical instrument having an end effector applying an acting force on a target by opening the end effector.

In this embodiment, the example in which the control is performed on only the manipulation in the opening direction in which the acting force increases is explained. In the same way of the third embodiment, in addition to the opening direction, the control may be performed in the closing direction of the pair of opening and closing members, which is the opposite direction. Similarly to the first embodiment, the order of the neutral zone and the pressing force increasing zone may be inverted.

While the embodiments of the invention have been described, the technical scope of the invention is not limited to the embodiments, but various modifications may be added to the elements or may be deleted, or the configurations of the embodiments may be combined without departing from the concept of the invention.

Figure 15:
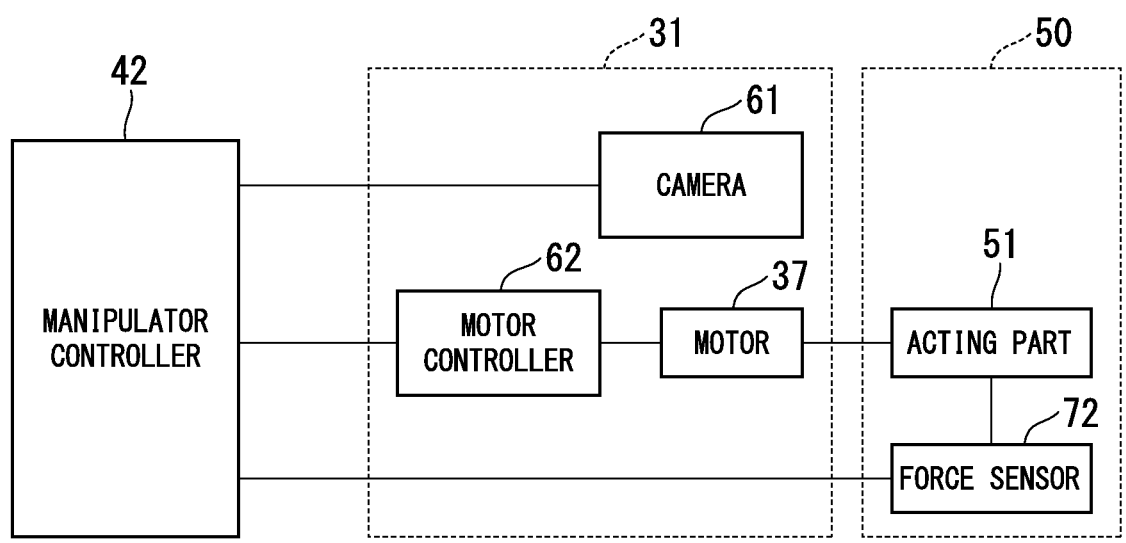
FIG. 15 is a block diagram illustrating the functional relation of a manipulator controller, a distal end of a slave arm, and a treatment tool in a medical master-slave manipulator according to a modified example of the invention.

For example, as shown in a modified example shown in FIG. 15, both the camera 61 and the force sensor 72 may be provided as the grip detecting unit. In this case, when determining whether the acting part comes in contact with a target, the manipulator controller appropriately selectively uses the image acquired by the camera 61 and the detection value of the force sensor 72 to be used or performs the determination based on both information pieces. Accordingly, it is possible to perform a more appropriate control.

Two neutral zones may be set with the acting force increasing zone interposed therebetween. Particularly, when a neutral zone of a small angle range (for example, of about several degrees) is disposed between a zone such as the first zone in which the acting part comes in contact with a target and the acting force increasing zone, the neutral zone serves as a "margin" and a non-gripped state can be smoothly transferred to a gripped state, thereby improving the operational feeling.

When the neutral zone precedes the acting force increasing zone after the acting part comes in contact with a target, it may be difficult to see the boundary between the neutral zone and the acting force increasing zone. Accordingly, when the amount of manipulation of the manipulation unit reaches the boundary, a signal which can be recognized by the operator may be sent. The type of the signal is not particularly limited, but all the types of signals such as a visual signal of light or the like, an auditory signal of sound or the like, and a signal for causing the movement of the opening and closing members to be heavier for a quick moment can be used.

Similarly, when the neutral zone is set subsequent to the acting force increasing zone and a signal which can be recognized by an operator is sent at the boundary between the acting force increasing zone and the neutral zone, the operator does not manipulate the manipulation unit to the limit to further increase the acting force even in the neutral zone. As a result, it is possible to suppress an unnecessary manipulation.

The surgical instrument according to the embodiments of the invention is not limited to the master-slave manipulators described in the above-mentioned embodiments. The surgical instrument according to the invention may be applied to, for example, a surgical instrument in which the manipulation part and the end effector are disposed in the same body and a remote manipulation is not performed.

The manipulation unit is not limited to the configuration having a pair of opening and closing members. For example, a configuration including a manipulation member which can get closer to and be separated from a base and opening and closing the acting part by bringing the manipulation member closer to and separated from the base may be used. Various manipulations such as a sliding manipulation, a twisting manipulation, and a pushing manipulation in the first direction and the second direction may be employed instead of the closing manipulation and the opening manipulation.

The maximum value of the acting force may be set to a desired value through the use of various input mechanisms such as a switch or a dial or a user interface displayed on the display unit.

While preferred embodiments of the present invention have been described, the present invention is not limited to the embodiments.

Additions, omissions, substitutions, and other variations may be made to the present invention without departing from the spirit and scope of the present invention. The present invention is not limited by the above description, but by the appended claims.

The invention claimed is:

1. A surgical instrument comprising:
an end effector that is opened and closed;
a manipulation unit which has an opening and closing member that is capable of opening and closing and which is configured to open and close the end effector by manipulating the opening and closing member in a first direction by a user so that the end effector applies an acting force to a target;
a grip detecting unit configured to acquire an information to determine whether the end effector applies the acting force to the target;
a driving unit configured to drive the end effector to be opened and closed; and
a control unit configured to control the driving unit based on the information input to the manipulation unit,
wherein when the control unit determines that the end effector applies the acting force to the target based on the information acquired by the grip detecting unit, the control unit:
sets an acting force increasing zone of a predetermined range in a first movable range in the first direction of the opening and closing member,
sets a neutral zone in a remaining area of the first movable range,
controls the driving unit so that the acting force increases with a constant gradient with respect to an amount of manipulation of the manipulation unit in the acting force increasing zone, and
controls the driving unit so that the acting force is kept constant and non-zero regardless of the amount of manipulation of the manipulation unit in the neutral zone.

2. The surgical instrument according to claim 1, wherein the acting force increasing zone is set in an initial area toward the first direction in the first movable range.

3. The surgical instrument according to claim 1, wherein the grip detecting unit includes a camera imaging the end effector.

4. The surgical instrument according to claim 1, wherein the grip detecting unit includes a force sensor detecting the acting force.

5. The surgical instrument according to claim 1, wherein the first movable range of the manipulation unit is set to be greater than a movable range of the end effector.

6. The surgical instrument according to claim 2, wherein the acting force decreases when the opening and closing member is manipulated in a second direction, and
wherein when the opening and closing member is manipulated in the second direction, the control unit
sets an acting force decreasing zone of a predetermined range to an initial area toward the second direction in a second movable range of the second direction of the manipulation unit, and
controls the driving unit so that the acting force decreases with a constant gradient with respect to the amount of manipulation of the manipulation unit in the acting force decreasing zone.

7. A control method of a surgical instrument having an end effector that is opened and closed and a manipulation unit which has an opening and closing member that is capable of opening and closing and which is configured to open and close the end effector by manipulating the opening and closing member in a first direction by a user so that the end effector applies an acting force to a target, the control method comprising:
repeatedly determining whether the end effector applies the acting force to the target;
when determining that the end effector applies the acting force to the target,
setting an acting force increasing zone of a predetermined range in a first movable range in the first direction of the opening and closing member,
setting a neutral zone in a remaining area of the first movable range;
causing the acting force to increase with a constant gradient with respect to an amount of manipulation of the manipulation unit in the acting force increasing zone; and
causing the acting force to be kept constant and non-zero regardless of the amount of manipulation of the manipulation unit in the neutral zone.

* * * * *